United States Patent
deLong et al.

(10) Patent No.: US 6,410,780 B1
(45) Date of Patent: *Jun. 25, 2002

(54) C11 OXYMYL AND HYDROXYLAMINO PROSTAGLANDINS USEFUL AS MEDICAMENTS

(75) Inventors: Mitchell Anthony deLong, West Chester; Jack Snyder Amburgey, Jr., Loveland; John August Wos; Biswanath De, both of Cincinnati; David Lindsey Soper, Monroe, all of OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/647,381

(22) PCT Filed: Mar. 22, 1999

(86) PCT No.: PCT/IB99/00478

§ 371 (c)(1),
(2), (4) Date: Sep. 28, 2000

§ 102(e) Date: Sep. 28, 2000

(87) PCT Pub. No.: WO99/50241

PCT Pub. Date: Oct. 7, 1999

Related U.S. Application Data

(60) Provisional application No. 60/080,075, filed on Mar. 31, 1998.

(51) Int. Cl.[7] .................. C07C 69/74; A61K 31/215
(52) U.S. Cl. .................. 560/121; 514/381; 514/438; 514/460; 514/530; 514/573; 548/251; 548/252; 548/254; 549/76; 549/494; 549/495; 562/503
(58) Field of Search .................. 562/503; 514/573, 514/530, 438, 461, 381; 560/121; 549/76, 494, 495; 548/251, 252, 254

(56) References Cited

U.S. PATENT DOCUMENTS

| | | |
|---|---|---|
| 3,776,938 A | 12/1973 | Bergstrom et al. |
| 4,011,262 A | 3/1977 | Hess et al. |
| 4,024,179 A | 5/1977 | Bindra et al. |
| 4,128,720 A | 12/1978 | Hayashi et al. |

FOREIGN PATENT DOCUMENTS

| | | |
|---|---|---|
| DE | 001801750 | 7/1969 |
| DE | 002460990 | 7/1976 |
| JP | 02 022226 | 1/1990 |
| WO | WO 90/02553 | 3/1990 |

OTHER PUBLICATIONS

P.W. Collins, et al., "Synthesis of Therapeutically Useful Prostaglandin and Prostacyclin Analogs", *Chem. Rev.*, vol. 93, pp. 1533–1564, (1993).

G.L. Bundy, et al., "Synthesis of 17–Phenyl–18, 19, 20–Trinorprostaglandins: 1 The PG Series", *Prostaglandins*, vol. 9, No. 1, pp. 1–4, (1975).

W. Bartman, et al., "Leutolytic Prostaglandins Synthesis and Biological Activity", *Prostaglandins*, vol. 17, No. 2, pp. 301–311, 1979.

C. Liljebris, et al., "Derivatives of 17–Phenyl–18, 19, 20–Trinoprostaglandins $F_{2\alpha}$ Isopropyl Ester: Potential Antiglaucoma Agents", *J. Med. Chem.*, vol. 38, No. 2, pp. 289–304, (1995).

F.A. Fitzpatrick, "Separation of Prostaglandins and Thromboxanes by Gas Chromatography with Glass Capillary Columns", *Analytical Chemistry*, vol. 50, No. 1, pp. 47–52, (1978).

K.A. Waddell, et al., "Combined Capillary Column Gas Chromatography Negative Ion Chemical Ionization Mass Spectrometry of Prostanoids", *Biomed. Mass Spectrom.*, vol. 10, No. 2, pp. 83–88, (1983).

*Primary Examiner*—Shailendra Kumar
(74) *Attorney, Agent, or Firm*—David V. Upite; James C. Kellerman; Carl J. Roof

(57) ABSTRACT

The invention provides novel prostaglandin analogs. In particular, the present invention relates to compounds having a structure according to formula (I) wherein $R_1$, $R_2$, $R_3$, $R_4$, $R_5$, $R_6$, W, X, Z, a, b, p and q are defined below. This invention also includes optical isomers, diastereomers and enantiomers of formula (I), and pharmaceutically-acceptable salts, biohydrolyzable amides, esters, and imides thereof. The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using these compounds or the compositions containing them.

(I)

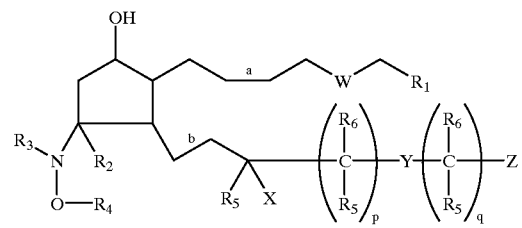

24 Claims, No Drawings

C11 OXYMYL AND HYDROXYLAMINO PROSTAGLANDINS USEFUL AS MEDICAMENTS

This application is a 371 of PCT/IB 99/00478,filed Mar. 22, 1999, which claim benefit of No. 60/080,075, Mar. 31, 1998.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB, PGE, PGF, and PGI) are C-20 unsaturated fatty acids. $PGF_{2a}$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_{2a}$ has the following formula:

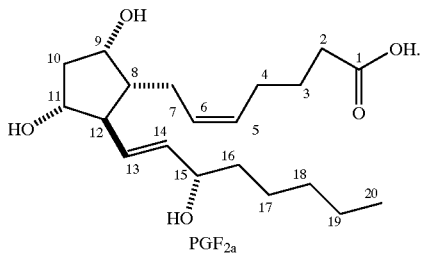

$PGF_{2a}$

Analogs of naturally occurring Prostaglandin F have been disclosed in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.* Vol. 93 (1993), pp. 1533–1564; G. L. Bundy and F. H. Lincoln, "Synthesis of 17-Phenyl-18,19,20-Trinorprostaglandins: I. The $PG_1$ Series", *Prostaglandins*, Vol. 9 No. 1 (1975), pp. 1–4; W. Bartman, G. Beck, U. Lerch, H. Teufel, and B. Scholkens, "Luteolytic Prostaglandins: Synthesis and Biological Activity", *Prostaglandins*, Vol. 17 No. 2 (1979), pp. 301–311; C. liljebris, G. Selen, B. Resul, J. Sternschantz, and U. Hacksell, "Derivatives of 17-Phenyl-18,19,20-trinorprostaglandin F2α Isopropyl Ester: Potential Antiglaucoma Agents", *Journal of Medicinal Chemistry*, Vol. 38 No. 2 (1995), pp. 289–304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_{2a}$ has also been shown to be a stimulator of bone resorption but not as potent as $PGE_2$. Also, it has been demonstrated that $PGF_{2a}$ has little effect on bone formation as compared to $PGE_2$. It has been suggested that some of the effects of $PGF_{2a}$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

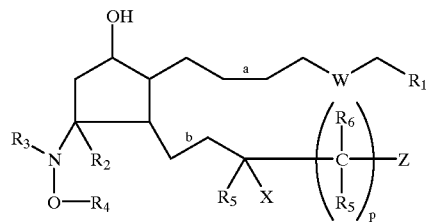

wherein $R_1$, $R_2$, $R_3$, $R_4$, $R_5$, $R_6$, W, X, Z, a, b, and p are defined below.

This invention also includes optical isomers, diastereomers and enantiomers of the formula above, and pharmaceutically-acceptable salts. biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Acyl" is a group suitable for acylating a nitrogen atom to form an amide or carbamate or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred substituted alkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Aromatic ring" is an aromatic hydrocarbon ring. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred aromatic rings include naphthyl and phenyl. The most preferred aromatic ring is phenyl.

"Bone disorder" means the need for bone repair or replacement. Conditions in which the need for bone repair or replacement may arise include: osteoporosis (including post menopausal osteoporosis, male and female senile osteoporosis and corticosteroid induced osteoporosis), osteoarthritis, Paget's disease, osteomalacia, multiple myeloma and other forms of cancer, prolonged bed rest, chronic disuse of a limb, anorexia, microgravity, exogenous and endogenous gonadal insufficiency, bone fracture, non-union, defect, prosthesis implantation and the like.

"Carbocyclic aliphatic ring" is a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1-C_{12}$; more preferred are $C_1-C_6$; more preferred still are $C_1-C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Heteroaromatic ring" is an aromatic ring containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 in the ring. Heteroaromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo, haloalkyl, and phenyl. Preferred heteroaromatic rings include thienyl, thiazolo, purinyl, pyrimidyl, pyridyl. and furanyl. More preferred heteroaromatic rings include thienyl, furanyl, and pyridyl. The most preferred heteroaromatic ring is thienyl.

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 in the ring. Bicyclic heterocyclic aliphatic rings contain from 8 to 12 member atoms, preferably 9 or 10 in the ring. Heterocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred heterocyclic aliphatic rings include piperzyl, morpholinyl, tetrahydrofuranyl, tetrahydropyranyl and piperdyl.

"Lower alkyl" is an alkyl chain comprised of 1 to 6, preferably 1 to 4 carbon atoms.

"Phenyl" is a monocyclic aromatic ring which may or may not be substituted with from about 1 to about 4 substituents. The substituents may be fused but not bridged and may be substituted at the ortho, meta or para position on the phenyl ring, or any combination thereof. The substituents may be halo, cyano, alkyl, heteroalkyl, haloalkyl, phenyl, phenoxy or any combination thereof. Preferred substituents on the phenyl ring include halo and haloalkyl. The most preferred substituent is halo. The preferred substitution pattern on the phenyl ring is ortho or meta. The most preferred substitution pattern on the phenyl ring is meta.

COMPOUNDS

The subject invention involves compounds having the following structure:

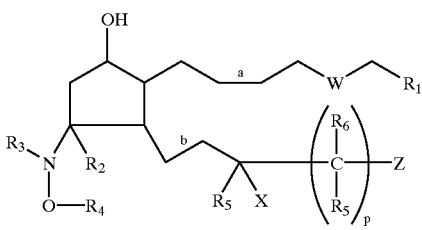

In the above structure, $R_1$ is $CO_2H$, $C(O)NHOH$, $CO_2R_7$, $CH_2OH$, $SO_2R_7$, $C(O)NHR_7$, $C(O)NHS(O)_2R_7$, or tetrazole; wherein $R_7$ is alkyl, heteroalkyl, monocyclic carbocyclic aliphatic ring, monocyclic heterocyclic aliphatic ring, monocyclic aromatic ring, or monocyclic heteroaromatic ring. Preferred $R_7$ is methyl, ethyl, and isopropyl. Preferred $R_1$ is $CO_2H$, $C(O)NHOH$, $CO_2R_7$, $C(O)NHSO_2R_7$, and tetrazole. Most preferred $R_1$ is $CO_2H$ and $CO_2R_7$.

In the above structure, W is O, NH, S, S(O), $S(O)_2$, or $(CH_2)_m$; wherein m is an integer from 0 to about 3. Preferred W is O and $(CH_2)_m$. Most preferred W is $(CH_2)_1$.

In the above structure, $R_2$ is H and $R_3$ is H or lower alkyl, or $R_2$ and $R_3$ together form a covalent bond.

In the above structure, $R_4$ is H, alkyl, heteroalkyl, monocyclic carbocyclic aliphatic ring, monocyclic heterocyclic aliphatic ring, monocyclic aromatic ring, or monocyclic heteroaromatic ring, provided that when each $R_5$ and $R_6$ is H, $R_4$ is other than methyl. Preferred $R_4$ is H and lower alkyl. Most preferred $R_4$ is H.

In the above structure, each $R_5$ is independently selected from the group consisting of H, $CH_3$, and $C_2H_5$. Preferred $R_5$ is H and $CH_3$. Most preferred $R_5$ is H.

In the above structure, X is $NHR_8$ or $OR_8$, wherein each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring. Preferred $R_8$ is H. Preferred X is $OR_8$. Most preferred X is OH.

In the above structure, each $R_6$ is independently selected from the group consisting of H, $CH_3$, $C_2H_5$, $OR_8$, and $NHR_8$. Preferred $R_6$ is H, $CH_3$, $C_2H_5$, $OR_8$. Most preferred $R_6$ is H and $CH_3$.

In the above structure, Z is H, methyl, monocyclic carbocyclic aliphatic ring, monocyclic heterocyclic aliphatic ring, monocyclic aromatic ring, or monocyclic heteroaromatic ring, bicyclic carbocyclic aliphatic ring, bicyclic heterocyclic aliphatic ring, bicyclic aromatic ring, or bicyclic heteroaromatic ring. Preferred Z is monocyclic aromatic ring and monocyclic heteroaromatic ring. More preferred Z is thienyl and phenyl.

In the above structure, a and b are independently selected from the group consisting of single bond, cis double bond, and trans double bond. Preferred a is single bond or cis double bond. Preferred b is single bond or trans double bond. When Z is H or methyl, preferred a is cis or trans double bond, preferably cis, and preferred b is cis or trans double bond, preferably trans.

In the above structure, p is an integer from 0 to about 6, preferably 2 or 3, most preferably 2.

The invention also includes optical isomers, diastereomers and enantiomers of the above structure. Preferred stereochemistry at all stereocenters of the compounds of the invention mimic that of naturally occurring $PGF_{2\alpha}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase in trabecular number through formation of new trabeculae; (2) An increase in bone mass and bone volume while maintaining a more normal bone turnover rate; and/or (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. liljebris, G. Selen, B. Resul, J. Sternschantz, and U. Hacksell, "Derivatives of 17-Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Compounds useful in the subject invention can be made using conventional organic syntheses. A particularly preferred synthesis is the following general reaction scheme:

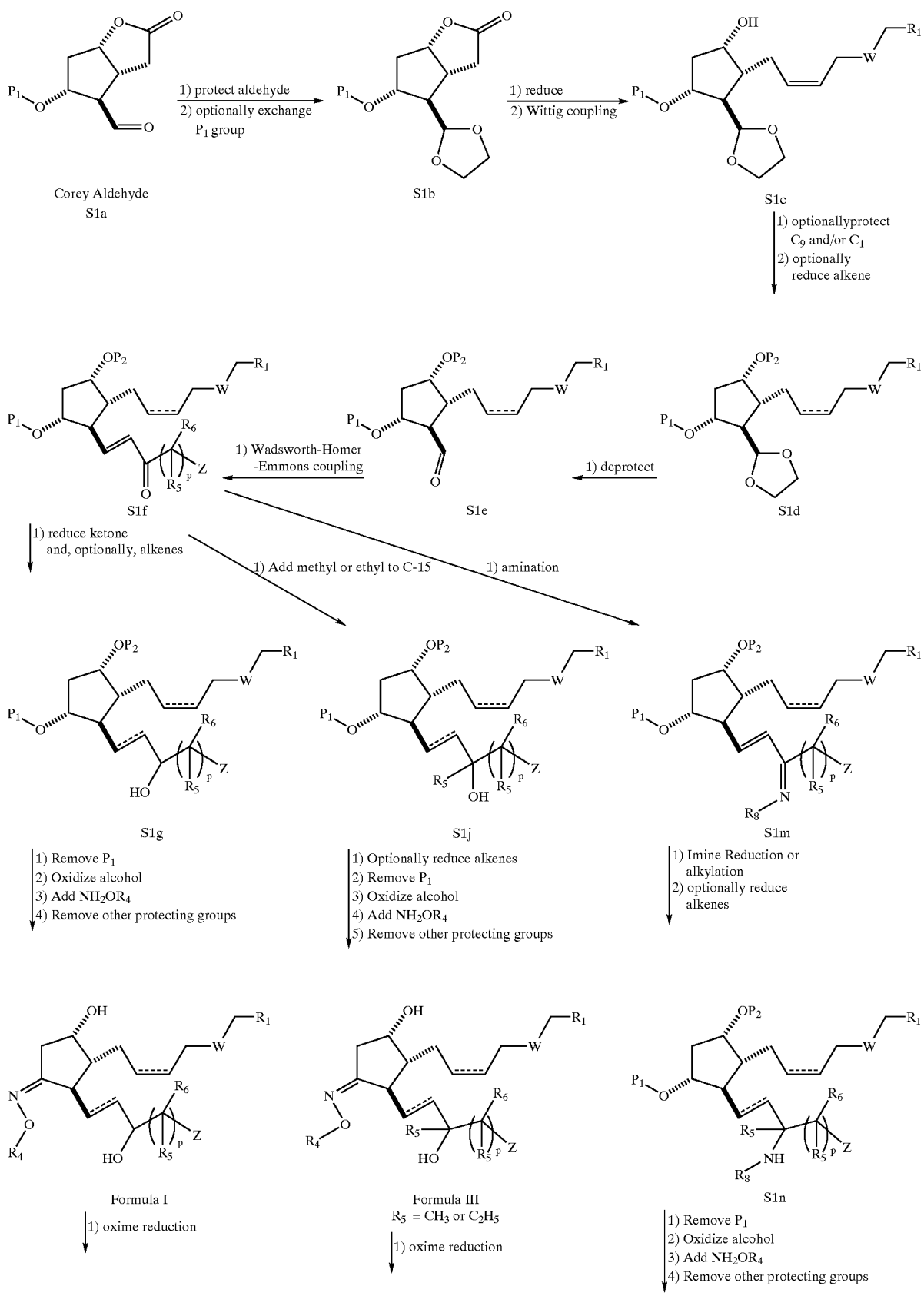

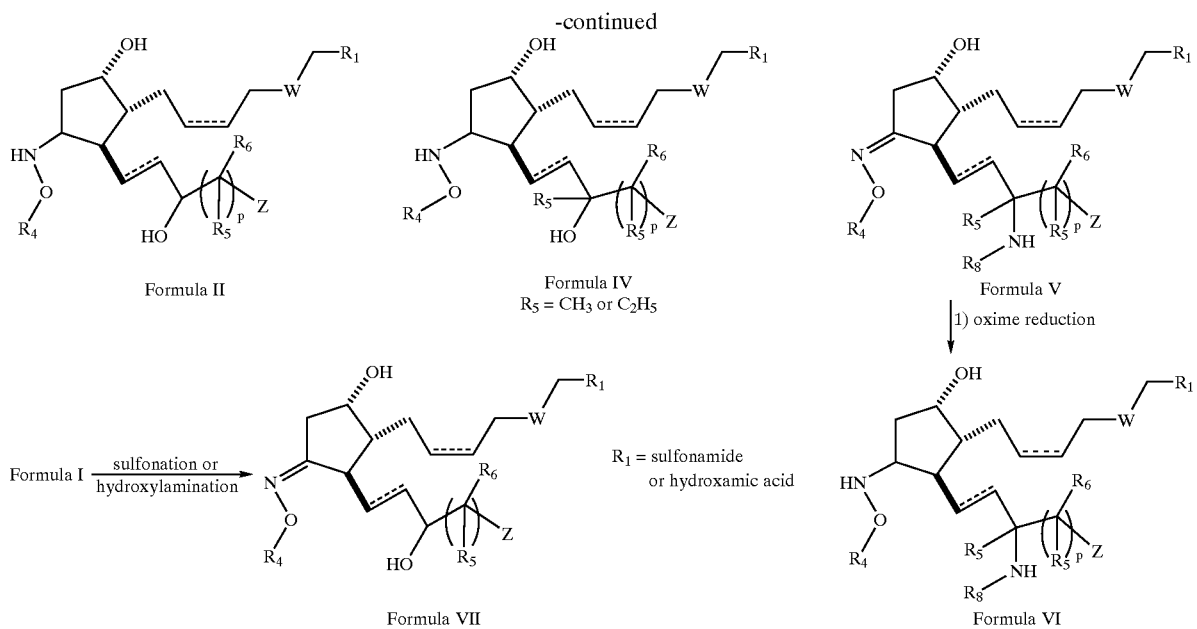

In Scheme 1, $R_1$, $R_2$, $R_3$, $R_4$, $R_5$, $R_6$ W, X, Z, and P are as defined above unless defined otherwise. The Corey Aldehyde (S1a) depicted as starting material for Scheme 1 is commercially available (such as from Aldrich Chemical or Cayman Chemical).

In the above Scheme 1, Corey Aldehyde is commercially-available with either a silyl group ($P_1$) or an ester group ($P_1$) attached to the alcohol. The preferred protecting groups include tert-butyldimethylsilyl, acetate, benzoate, and para-phenyl benzoate. The most preferred protecting group is tert-butyldimethylsilyl.

The Corey aldehyde (S1a) is first reacted with an aldehyde protecting group to make a ketal or acetal. Examples of this type of protection are found in Greene and Wuts, *Protecting Groups in Organic Synthesis*, 2d ed., Wiley & Sons, N.Y. 1991. In this case, especially preferred are cyclic ketals and acetals. The aldehyde (S1a) is reacted with the appropriate 1,2-diol and a suitable acidic catalyst. The solvent can be the diol, and an anhydrous solvent, such as ether or dichloromethane. Particularly useful is 1,2-bis-TMS ethylene glycol to effect this transformation in ether at room temperature.

The ketal-protected S1a may then undergo a routine of protection/deprotection if desired, to exchange the $P_1$ group for a more suitable one, using procedures known in the art. Particularly useful is the exchange of a silyl group for an acyl group, and vice versa. Also useful is the exchange of a silyl or acyl group for an o-bromo-benzyl ether group.

The compound (S1b) is then subjected to a DIBAL reduction to make the hemiacetal. This intermediate is not isolated but reacted as soon as possible with a Wittig salt to form an alkene (S1c). Particularly preferred Wittig salts are derived from omega bromo- four to five carbon straight chain carboxcyclic acids and 3-oxo-carboxcyclic acids. These are conveniently combined with triphenylphosphine in a suitable solvent to form the reactive Wittig salts. Other preferred reagents include straight chain omega-bromo tetrazoles and primary nitrites.

The alkene (S1c) is typically not isolated, but reacted crude with diazomethane in diethyl ether or, preferably, with TMS diazomethane in methanol to give S1d. In addition, a suitable protecting group may be placed on the $C_9$ alcohol and/or the alkene may be reduced at this time. The compound S1d is isolated by methods known to one of ordinary skill in the art. Such methods include, but are not limited to, extraction, solvent evaporation, distillation, and crystallization. Preferably, it is purified by flash chromatography on silica gel (Merck, 230–400 mesh) using 10% EtOAc/hexanes as the eluent.

The cyclic ketal of S1d is removed with acid or acidic ion exchange resin in a suitable solvent to give the free aldehyde. Preferred solvents include THF/water mixtures. The resulting aldehyde (S1e) is not isolated but reacted with ketone-stabilized phosphonium salts. These are generally referred to as "Wadsworth-Horner-Emmons" reagents. This reaction requires a mild base. Examples of suitable bases include sodium carbonate or triethyl amine. The product ketone (S1f) is purified by methods known to one of ordinary skill in the art. Such methods include, but are not limited to, extraction, solvent evaporation, distillation, and crystallization. Preferably, the ketone (S1f) is purified by flash chromatography on silica gel (Merck, 230–400 mesh) using 20% EtOAc/hexanes as the eluent.

As seen in Scheme 1 above, the ketone (S1f) can be reacted in three ways. Reduction of the ketone with a reducing agent such as the Luche reagent, effects an alcohol at C-15, as illustrated by S1g.

At this point, the alcohols of S1g at C-9 and C-15 may be protected, if needed or desired. If so, the alcohols can be protected as described previously herein. The S1g compound containing protected or unprotected alcohols is then treated with a deprotecting agent to release selectively $P_1$, on C-11. Examples of such selective deprotection reactions are given in Greene and Wuts.

Alternatively, when $P_1$ is the o-bromobenzyl ether, reduction of the bromine with a radical reducing agent such as $(n-Bu)_3SnH$ will cause the radical-induced oxidation of C-11 to the ketone without needing protection. In addition, some PGD analogs are commercially-available with this oxidation at C-11. These compounds can be directly taken on from this step.

Compounds of the type S1g can be converted into compounds of Formula I by the addition of hydroxylamine or alkyoxyamines. After this addition, removal of protecting groups, if any, yields compounds of Formula I. Compounds depicted by Formula I are exemplified in Examples 1–25 and 28–34.

Compounds of Formula I may be converted into compounds of Formula II by reducing the oxime bond with a selective reducing agent. The preferred reducing agent is sodium cyanoborohydride. Compounds depicted by Formula II are exemplified in Examples 35–36 and 38–40.

The ketone (S1f) can also be converted into compounds of the type S1j. This occurs by the addition of suitable nucleophile to the ketone (S1f). Examples of nucleophiles include methyl magnesium bromide. Using substantially the same techniques described above, the compounds of the type S1j can be converted into compounds of Formula III, and compounds of Formula III can be converted into compounds of Formula IV. Compounds depicted by Formula III are exemplified in Examples 26–27 and 41–43, and compounds depicted by Formula IV are exemplified in Examples 37 and 44.

Compounds of the type S1f can also be reacted to give compounds of the type S1m by reacting the ketone at C-15 with an active amine. Examples of reactive amines include methyl amine and ethyl amine. The products can be reduced or can react with nucleophiles using standard techniques, and the reduction can also extend to reduce the alkenes, if desired, using a reagent such as hydrogen gas over palladium on carbon. Alternatively, sodium cyanoborohydride will selectivity reduce the imine without disrupting the alkenes. Finally, a suitable nucleophile, preferably such as a methyl cerium reagent, can add to the imine. Addition of the methylcerium nucleophile (~1.5 equiv.) is described in T. Imamoto, et al., "Carbon-Carbon Bond Forming Reactions Using Cerium Metal or Organocerium (III) Reagents", *J. Org. Chem.* Vol. 49 (1984) p. 3904–12; T. Imamoto, et al., "Reactions of Carbonyl Compounds with Grignard Reagents in the Presence of Cerium Chloride",*J. Am. Chem. Soc.* Vol. 111 (1989) p. 4392–98; and references cited therein, gives the aminomethyl derivative. In that case, $R_5$ in compound S1n would be a methyl group.

Using the reactions disclosed above for compounds of the type S1g, compounds of Formula V can be made from S1n. Compounds depicted by Formula V are exemplified in Example 45. Compounds of the Formula VI can thus be made from compounds of Formula V. Compounds depicted by Formula VI are exemplified in Examples 46.

Compounds of Formula VII can be made from sulfonation or hydroxylamination of compounds of Formula I. Compounds depicted by Formula VII are exemplified in Examples 47–48.

These compounds are isolated by methods known to one of ordinary skill in the art. Such methods include, but are not limited to, extraction, solvent evaporation, distillation, and crystallization.

The following non-limiting examples illustrate the compounds, compositions, and uses of the present invention.

EXAMPLES

Compounds are analyzed using $^1$H and $^{13}$C NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh; J. T. Baker) and visualized using uv light, 5% phosphomolybdic acid in EtOH, or ammonium molybdate/cerric sulfate in 10% aqueous $H_2SO_4$.

Example 1

Preparation of 11-oxymyl-13,14-dihydro-17-(2-fluorophenyl) 17 trinor $PGD_1\alpha$ (1n):

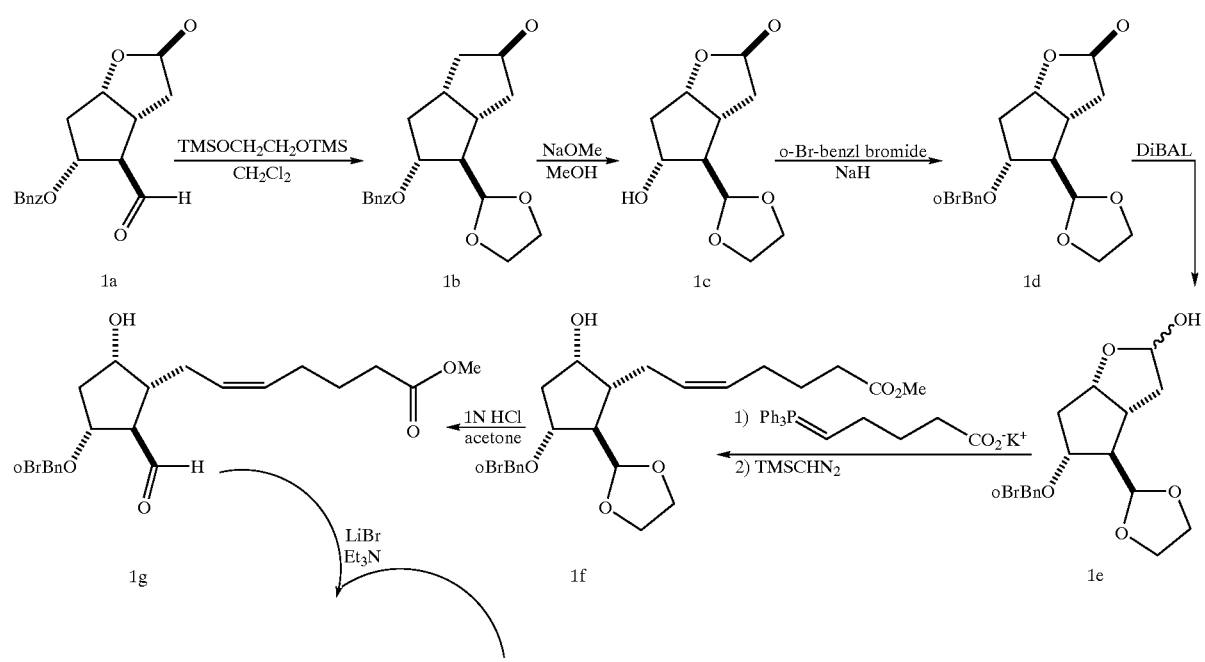

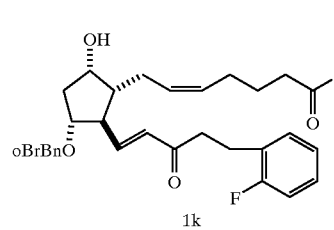
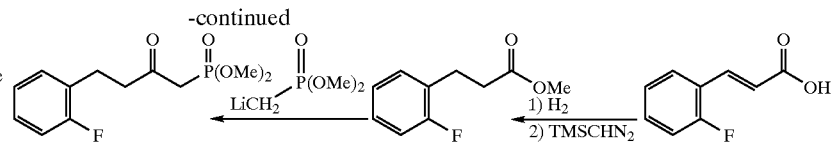
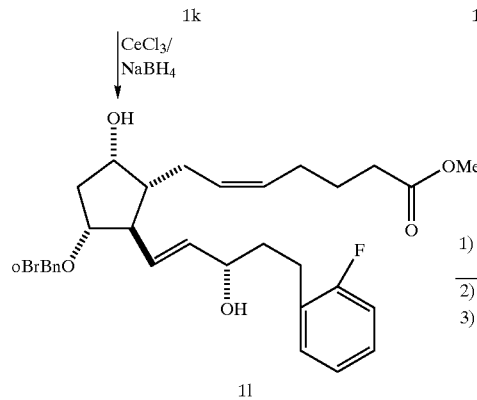
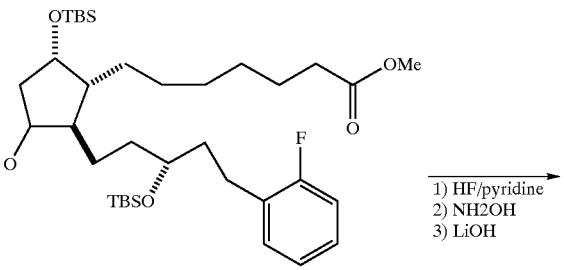
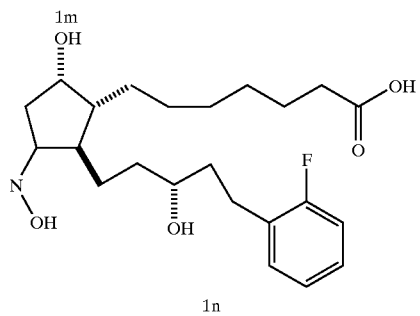

a. 7-benzoyloxy-6-(2,5-dioxolanyl)-2-oxabicyclo[3.3.0]octan-3-one (1b)

In a round bottom flask equipped with a magnetic stir bar is placed 1,2-bis(trimethylsilyloxy)ethane in methylene chloride at −78° C. To this is added, within 20 min., a solution of 1a in CH$_2$Cl$_2$. The reaction is stirred for 1 hour at −78° C. and then slowly warmed to 25° C. for 1 hour. The reaction is quenched at 0° C. with water, extracted with methylene chloride, dried over MgSO$_4$, and concentrated in vacuo to give crude 1b.

b. 6-(2,5-dioxolanyl)-7-hydroxy-2-oxabicyclo[3.3.0]octan-3-one (1c)

To a well stirred solution of crude 1b (63.85 g, 201 mmol, 1 eq) in methanol (786 mL) at 0° C. is added a suspension of sodium methoxide (13.27 g, 246 mmol, 1.2 eq) in MeOH (98.3 mL). The reaction is stirred at 0° C. for 1 hour and then is warmed to 25° C. for 1 hour. The reaction is neutralized with acidic ion exchange resin which has been washed thoroughly with MeOH (5×100 mL). The filtrate is concentrated in vacuo to give a syrup which is subjected to flash chromatography on silica gel eluting with 4:1 hexane:ethyl acetate and 2% MeOH in CH$_2$Cl$_2$ to give 1c as a yellow syrup.

c. 6-(2,5 dioxolanyl)-2-oxa-7-(o-bromobenzyloxy)bicyclo[3.3.0]octan-3-one (1d)

In a round bottom flask with a magnetic stir bar, is stirred a solution of 1c in CH$_2$Cl$_2$. To this solution is added dropwise at −78° C. a suspension of NaH. The reaction is stirred for 30 min. at −78° C. and then ortho-bromo benzyl bromide is added and the reaction is warmed to 25° C. overnight. The reaction is quenched with water (100 mL).

The organic layer is washed with water (3×100 mL), dried over MgSO$_4$, and concentrated in vacuo to give a yellow oil which is subjected to flash chromatography on silica gel eluting with hexanes then 1% MeOH in CH$_2$Cl$_2$. The product is then washed with 1N HCl, 0.1N HCl, water and brine to give 1d.

d. Methyl 7-(5-(2,5-dioxolanyl)-2-hydroxy-4-(o-bromobenzyloxy)cyclopentyl)hept-5-enoate (1f)

In a round bottom flask with a magnetic stir bar, is stirred a solution of 1d in dry toluene. To this solution, at −78° C., is slowly added DIBAL(diisobutyl aluminum hydride) in hexane. The reaction mixture is stirred for 2 hours and then warmed to 0° C. Saturated NH$_4$Cl is added to the reaction mixture which is then slowly warmed to 25° C. Diluted with water (100 mL), the insoluble precipitate is removed by suction filtration and the solid is washed with EtOAc (2×25 mL). The liquid phase is extracted with EtOAc (3×50 mL) and the combined organic phase is dried over MgSO$_4$ and concentrated in vacuo to give a yellow syrup. The product, 1e, must either be used immediately or stored at −70° C. overnight. To a suspension of (4-carboxybutyl)triphenylphosphonium in THF at 0° C. under Nitrogen is added dropwise a solution of KHMDS (potassium hexamethylsilazide) in toluene. The resulting deep orange colored reaction mixture is stirred for 1 hour at 25° C. To the reaction mixture above at −78° C. is added a solution of 1e in THF. The reaction mixture is allowed to warm to 25° C. overnight. The reaction is quenched with water at 0° C. and the pH is adjusted to 3.5–4.0 with 1N HCl. The water phase is extracted with EtOAc and the combined organic phase is dried over MgSO$_4$ and concentrated in vacuo to give a syrup containing crude acid. To a well stirred solution of the acid in MeOH at 0° C. is added trimethylsilane (TMS) diazomethane until the reaction mixture keeps a light yellow color. The addition of 1 drop of acetic acid, glacial and thin layer chromatography verifies the reaction has gone to completion. The reaction solution is concentrated in vacuo and is purified via flash chromatography on silica gel eluting with 30% EtOAc in hexanes yielding 1f.

e. Methyl 7-(2-hydroxy4-(o-bromobenzyloxy)-5-formyl-cyclopentyl)hept-5-enoate (1g)

In a round-bottomed flask with a magnetic stir bar is placed an amount of the ketal, 1f. To this flask is added a sufficient amount of a mixture of 2 parts acetone to 1 part 1N HCl to bring the ketal completely into solution. This material is stirred by TLC until the starting material is consumed, typically overnight. The crude mixture containing the product 1g is extracted with ether and the ether extract is re-esterified in situ with, preferably, TMS-diazomethane. The organic extracts are concentrated under reduced pressure at 0° C. and used immediately without further purification.

f. Methyl 3-(2-fluorophenyl)propionate (1i)

In a Parr® hydrogenation vessel is placed 2-fluorocinnamic acid (1h) (1.0 equiv) and palladium on carbon in a 1/1 methanol/ethyl acetate solution. The heterogeneous solution is placed on a Parr® shaker and treated with hydrogen (50 psi) until uptake has ceased. The mixture is filtered through Celite® and concentrated under reduced pressure. The residue is taken up in diethyl ether and is treated with diazomethane until the yellow color persists. The solution is concentrated under reduced pressure giving the crude methyl ester. Purification is effected by column chromatography on silica gel (hexane/ethyl acetate 5/1) to yield Methyl 3-(2-fluorophenyl)propionate (1i) in quantitative yield.

g. Dimethyl-4-(2-fluorophenyl)-2-oxo-butylphosphonate (1j)

In a flame-dried, round-bottomed flask equipped with a stir bar and thermometer is placed dimethylmethyl phosphonate (1.0 equiv.) in anhydrous THF. The solution is cooled to −78° C. and treated with n-butyllithium (1.05 equiv.). The reaction mixture is stirred for 15 minutes. To this solution is added methyl-3-(2-fluorophenyl)propionate (1.1 equiv.) in anhydrous THF. The mixture is allowed to warm to room temperature over the next 6 hours. The mixture is treated with a saturated solution of ammonium chloride and extracted with CH$_2$Cl$_2$. The organic layer is washed with water followed by brine. The combined aqueous layers are back extracted with CH$_2$Cl$_2$ and the organic layers combined, dried over anhydrous MgSO$_4$, filtered, and concentrated under reduced pressure. Purification is effected by silica gel column chromatography (hexane/ethyl acetate/2-propanol 45/50/5 to hexane/ethyl acetate/2-propanol 40/50/10) to yield 1.34 g (70%) of dimethyl4-(2-fluorophenyl)-2-oxo-butylphosphonate (1j) as an oil.

h. 11-o-Bromobenzyloxy-17-(2-fluorophenyl)-17-trinor-15-oxo-PGF$_{2a}$ methyl ester (1k)

In a flame-dried, round-bottomed flask equipped with a magnetic stirbar is placed dimethyl-4-(2-fluorophenyl)-2-oxo-butylphosphonate (1j) (1.43 equiv) in DME and water. To this solution is added lithium bromide (1.65 equiv), triethylamine (1.65 equiv), and (1g) (1.0 equiv). The solution is stirred at room temperature for 48 hours. At this point additional triethylamine and water is added and the solution is stirred for an additional hour. The solution is poured into brine and extracted with 3 portions of ethyl acetate. The organic layers are combined, dried over anhydrous MgSO$_4$, filtered, and concentrated under reduced pressure. Purification is effected by silica gel column chromatography (dichloromethane/methanol 19/1) to give 11-o-bromobenzyloxy-17-(2-fluorophenyl)-17-trinor-15-oxo-PGF$_{2a}$ methyl ester (1k) as an oil.

i. 11-o-Bromobenzyloxy-15-(R,S)-17-(2-fluorophenyl)-17-trinor-PGF$_{2a}$ methyl ester (1l)

In a flame-dried round-bottomed flask equipped with a stir bar is placed 17-(2-fluorophenyl)-17-trinor-15-oxo-PGF$_{2a}$ methyl ester (1k) (1.0 equiv), cerium trichloride (1.05 equiv) in methanol. The solution is stirred at room temperature for 5 minutes. The solution is cooled to −10 C. and sodium borohydride (1.02 equiv.) in methanol is added. The solution is stirred at −10° C. for 3 hours. The mixture is treated with water and the pH brought to 6–7 with 1N hydrochloric acid. The mixture is extracted twice with ethyl acetate and the organic layers combined, dried over anhydrous MgSO$_4$, filtered and concentrated under reduced pressure. Purification is effected by silica gel column chromatography (3% methanol in dichloromethane to 5% methanol in dichloromethane) to give the 15 (R) epimer and the 15 (S) epimer as colorless oils.

j. 9,15-bis-tert-butyldimethylsilyloxy-13,14-dihydro-17-(2-fluorophenyl)-17-trinor-PGD$_1$ methyl ester (1m)

In a round-bottomed flask equipped with a magnetic stirbar, is stirred a solution of 1l (1 equiv) in CH$_2$Cl$_2$. To this solution is added dropwise at −78° C. 2,6-lutidine (2.9 equiv.) followed by TBDMSOTf (2.8 equiv.). The reaction is stirred for 30 minutes at −78° C. and then warmed to 25° C. overnight. The reaction is quenched with water. The organic layer is washed with water, dried over MgSO$_4$, and concentrated in vacuo to give a yellow oil which is subjected to flash chromatography on silica gel eluting with hexanes then 1% MeOH in CH$_2$Cl$_2$. The product is then washed with 1N HCl, 0.1N HCl, water, and brine to give the bis-protected intermediate. This intermediate is then placed in a flame-dried round-bottomed flask equipped with a stir bar. Added is palladium on carbon in ethyl acetate (3 mL). The heterogeneous mixture is treated with excess hydrogen via a balloon for 18 hours. The mixture is filtered through Celite® and is concentrated under reduced pressure to give 9,15-bis-tert-butyldimethylsilyloxy-13,14-dihydro-17-(2-fluorophenyl)-17-trinor-PGF$_{1a}$ methyl ester. Then 9,15-bis-tert-butyldimethylsilyloxy-13,14-dihydro-17-(2-fluorophenyl)-17-trinor-PGF a methyl ester is dissolved in dichloromethane and excess pyridinium chlorochromate is added. The reaction is monitored by TLC. As soon as the starting material is consumed. the material is filtered through Fluorosil® and chromatographed to yield the PGD analog 1m.

k. 11-oximyl-13,14-dihydro-17-(2-fluorophenyl)-17-trinor-PGD$_1$ (1n)

A round-bottomed flask equipped with a stirbar is cooled to 0° C. and the methyl ester (1m) and a solution of HF in pyridine are added. The solution is allowed to warm to room temperature and followed by TLC. Upon consumption of the starting material, the solution is concentrated and partitioned between ethyl acetate and 0.1% aqueous sodium carbonate. The organic extracts are combined and chromatographed and the crude product is stirred overnight with hydroxylamine and sodium acetate (1:9) in 1:1:3 p-dioxane:water:methanol. The mixture is concentrated under reduced pressure and added is lithium hydroxide monohydrate (1.8 equiv) in a 50/50 THF/water solution. The mixture is stirred at room temperature for 6 hours and then diluted with water and acidified to pH 2–3 with 1N HCl. The aqueous phase is extracted 3 times with ethyl acetate and the organic layers combined. The combined organic layers are dried over anhydrous MgSO$_4$, filtered, and concentrated under reduced pressure to yield the crude acid. Purification is effected by HPLC to yield an analytical sample of 1n.

Examples 2–24

Examples 2–24 are prepared using substantially the same procedures as those described in Example 1, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 2

11-oximyl-13,14-dihydro-17-(2,4-difluorophenyl)-17-trinor-PGD$_1$ methyl ester

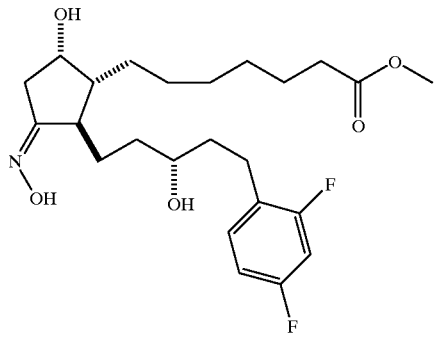

Example 3

11-oximyl-13,14-dihydro-17-(3,5-difluorophenyl)-17-trinor PGD$_1$

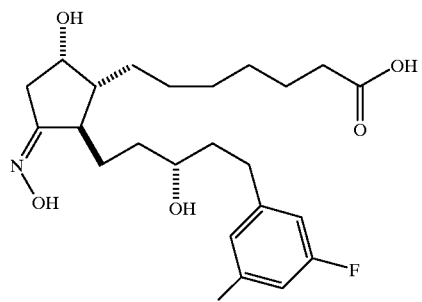

Example 4

11-oximyl-13,14-dihydro-17-(3-fluorophenyl)-17-trinor-PGD$_1$ methyl ester

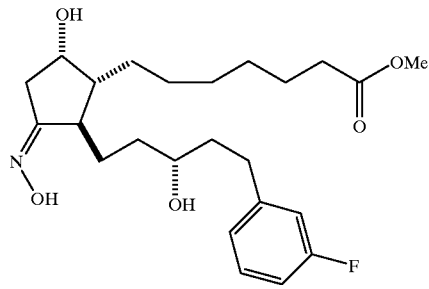

Example 5

11-oximyl-13,14-dihydro-17-(4-fluorophenyl)-17-trinor PGD$_1$ ethyl ester

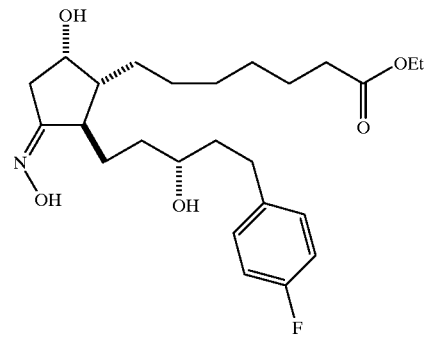

Example 6

11-oximyl-13,14-dihydro-17-(3-fluorophenyl)-17-trinor PGD$_1$

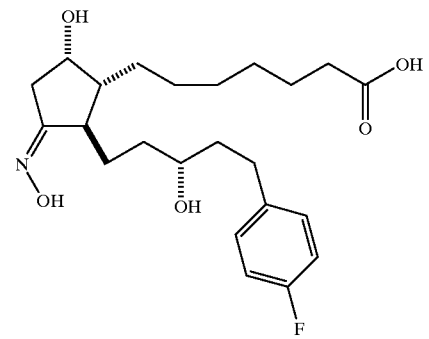

Example 7

11-oximyl-13,14-dihydro-17-(3-fluoro5-trifluoromethylphenyl)-17-trinor PGD$_1$

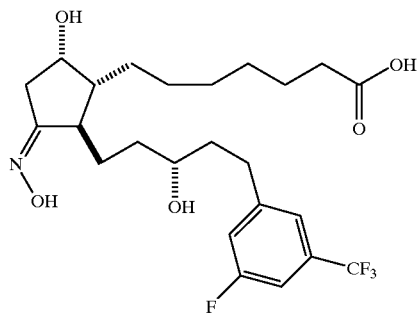

Example 8

11-oximyl-13,14-dihydro-16-methyl-17-(3fluorophenyl)-17-trinor PGD$_1$

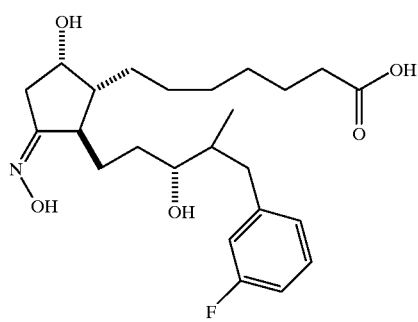

Example 9

11-oximyl-13,14-dihydro-17-(2-methoxyphenyl)-17-trinor PGD$_1$

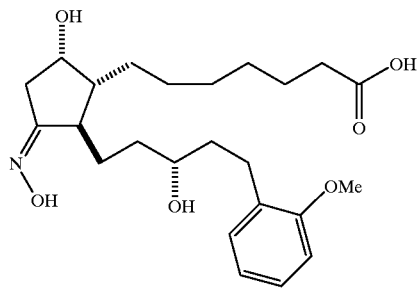

Example 10

11-oximyl-13,14-dihydro-17-(3-methoxyphenyl)-17-trinor PGD$_1$ isopropyl ester

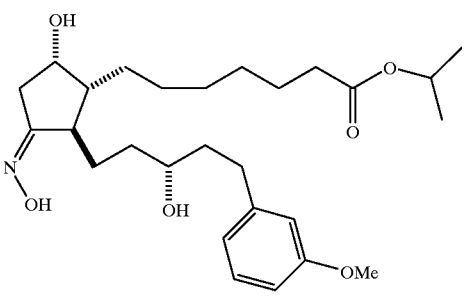

Example 11

11-oximyl-13,14-dihydro-18-(2-thienyl)-18-dinor PGD$_1$ methyl ester

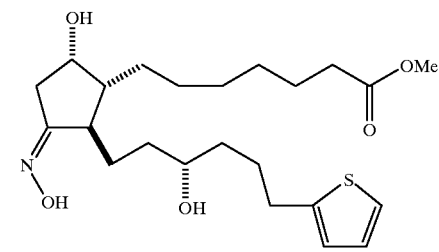

Example 12

11-oximyl-13,14-dihydro-17-((3-trifluoromethyl)phenyl)-17-trinor PGD$_1$ methyl ester

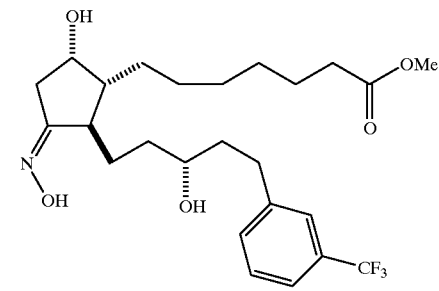

Example 13
11-oximyl-13,14-dihydro-17-(2-methylphenyl-17-trinor PGD$_1$ glyceryl ester
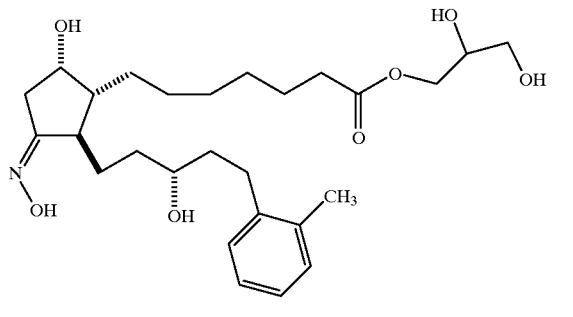
Example 14
11-oximyl-13,14-dihydro-17-(3-methylphenyl)-17-trinor PGD$_1$
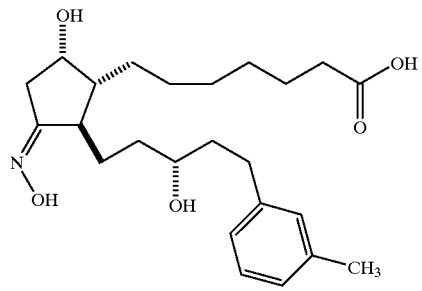
Example 15
11-oximyl-13,14-dihydro-17-phenyl-17-trinor PGD$_1$
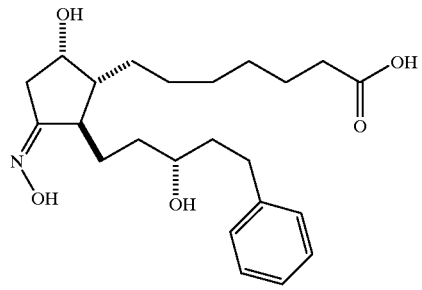
Example 16
11-oximyl-13,14-dihydro-18-(2-fluorophenyl)-18-dinor-PGD$_1$
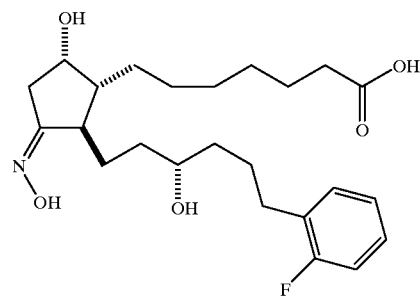
Example 17
11-oximyl-13,14-dihydro-18-(2-furanyl)-18-dinor-PGD$_1$
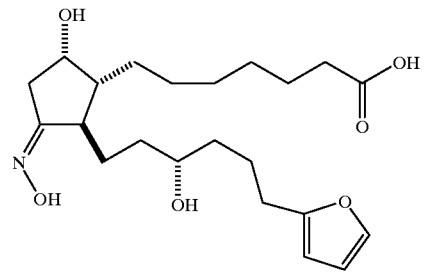
Example 18
11-oximyl-13,14-dihydro-17-(3-furanyl)-17-trinor-PGD$_1$
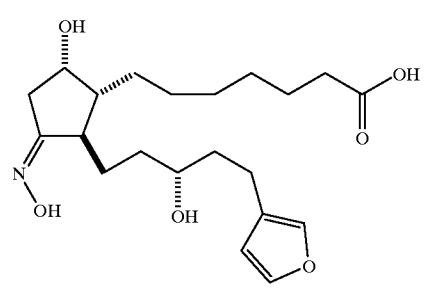

Example 19
11-oximyl-13,14-dihydro-17-(3-bromophenyl)-17-trinor-PGD$_1$
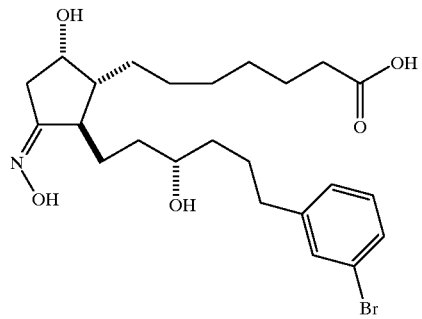
Example 20
11-methoximyl-13,14-dihydro-17-phenyl-17-trinor PGD$_1$
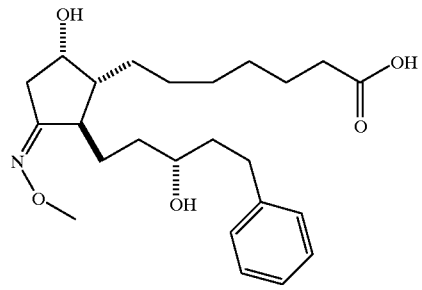
Example 21
11-methoximyl-13,14-dihydro-18-(2-fluorophenyl)-18-dinor-PGD$_1$
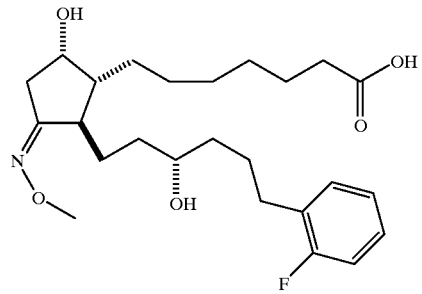
Example 22
11-methoximyl-13,14-dihydro-17-(3,5-difluorophenyl)-17-trinor PGD$_1$
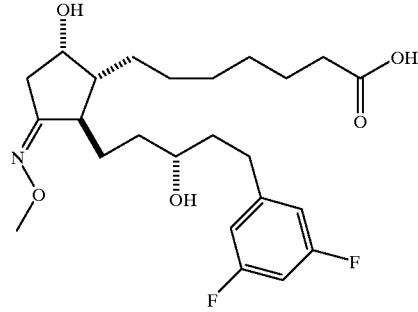
Example 23
11-ethoximyl-13,14-dihydro-17-(3,5-difluorophenyl)-17-trinor PGD$_1$
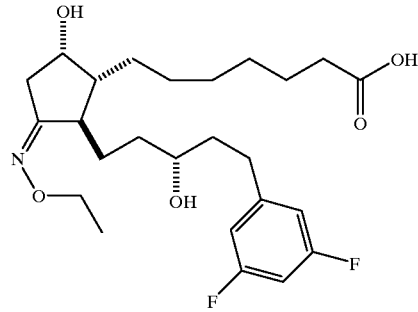
Example 24
11-t-butoximyl-13,14-dihydro-17-(3-fluorophenyl)-17-trinor PGD$_1$
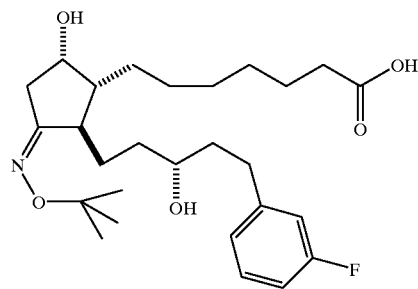

Example 25

11-oximyl-16,16-dimethyl-PGD$_2$

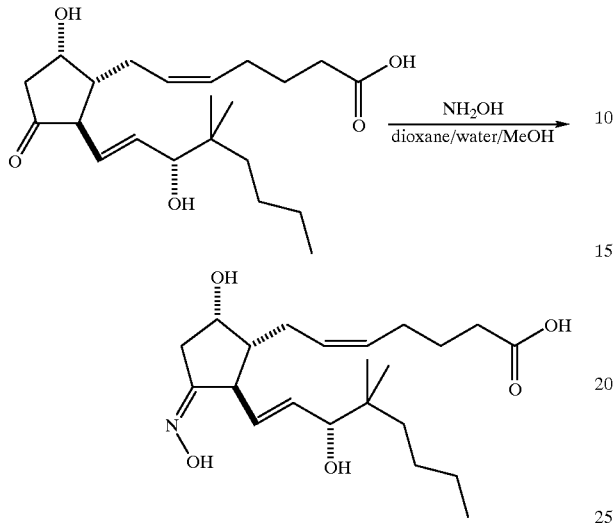

16,16-dimethyl PGD$_2$ (available from Cayman Chemical Co.) is subjected to hydroxylamine and sodium acetate (1:9) in 1:1:3 p-dioxane:water:methanol overnight, followed by isolation by HPLC, to yield 11-oximyl-16,16-dimethyl PGD$_2$.

Examples 26–31

Examples 26–31 are prepared using substantially the same procedure as that described in Example 25, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 26

11-oximyl-15-R-methyl-PGD$_2$

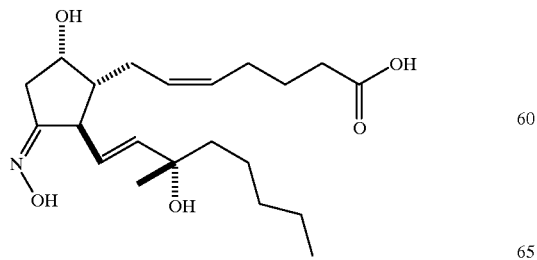

Example 27

11-oximyl-15-S-methyl-PGD$_2$

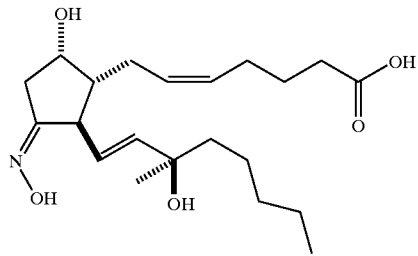

Example 28

11-oximyl-PGD$_1$

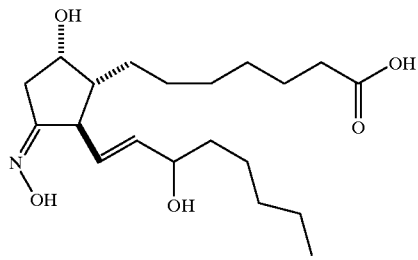

Example 29

11-oximyl-17-phenyl-17-trinor-PGD$_2$

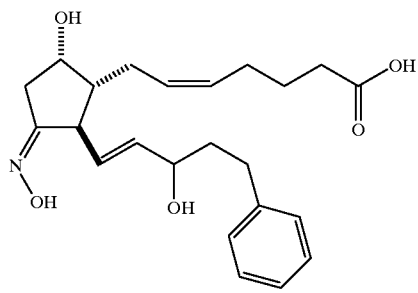

Example 30

11-oximyl-PGD$_1$ alcohol

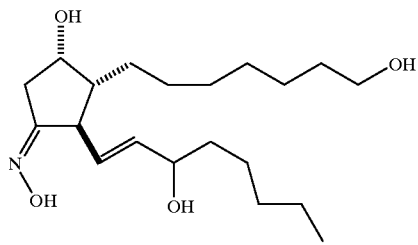

Example 31

11-oximyl-20-dihomo-PGD$_2$

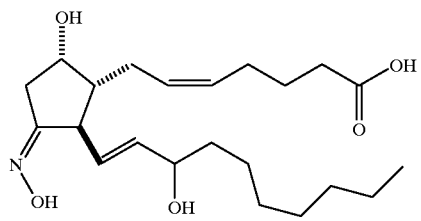

Example 32

11-oximyl-17-(o-fluorophenyl)-17-trinor-PGD$_2$

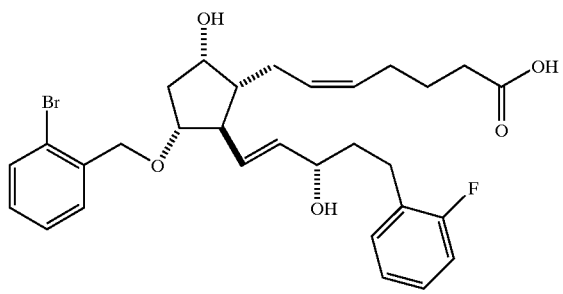

Example 33

11-oximyl-18-phenyl-18-dinor-PGD$_2$

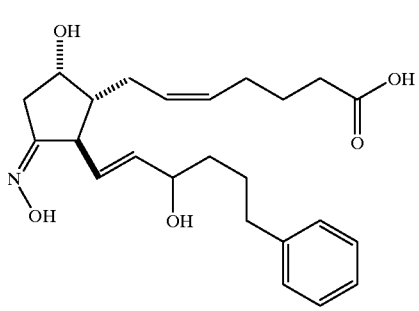

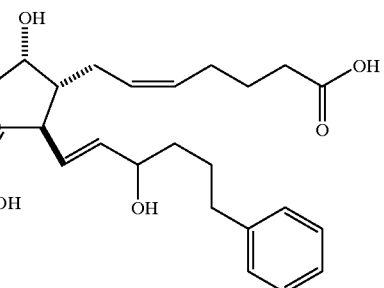

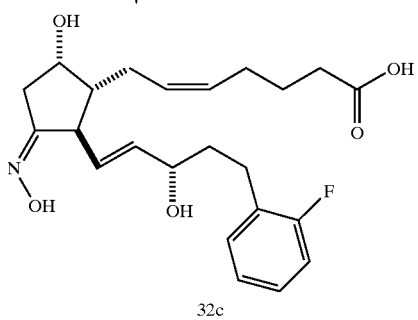

11-o-bromobenzyloxy-17-(o-fluorophenyl)-17-trinor-PGF$_{2\alpha}$ (1I from Example 1) is dissolved in benzene and 2.0 eq. of tri-n-butyl tin hydride is added, followed by 0.1 equiv. of AIBN. The solution is refluxed overnight, then concentrated and chromatographed to yield S32b. This ketone is then subjected to the standard hydroxylation conditions of Example 25, yielding S32c, 11-oximyl-17-(o-fluorophenyl)-17-trinor-PGD$_2$

Examples 33–34

Examples 33–34 are prepared using substantially the same procedure as that described in Example 32, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 34

11-oximyl-17-phenyl-17-trinor-1-tetrazolyl PGD$_2$

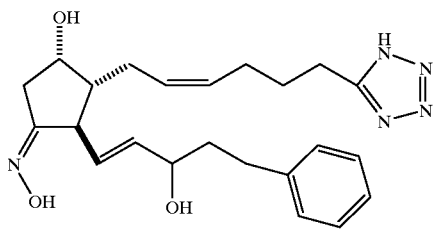

Example 35

11-hydroxylamino-17-phenyl-17-trinor-1-tetrazolyl PGF$_{2a}$

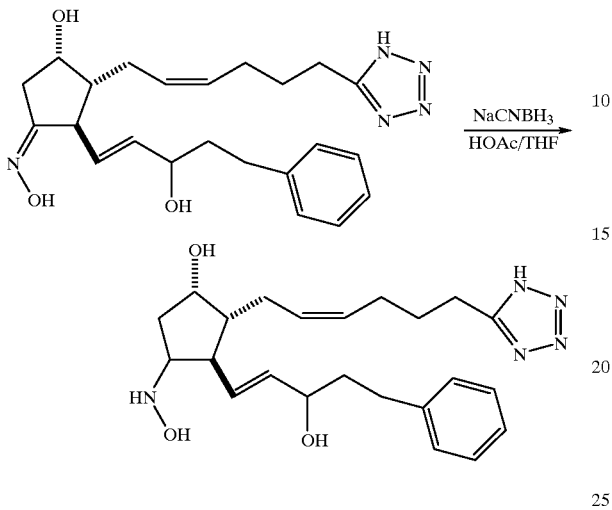

To a 500 mL round bottom flask is added 11-oximyl-17-phenyl-17-trinor-1-tetrazolyl PGD$_2$ (Example 34) and 1.5 equiv. of sodium cyanoborohydride in a 1:1 mixture of acetic acid and tetrahydrofuran. The reaction is monitored by TLC. After complete consumption of starting material, the reaction is diluted with water and exhaustively extracted with EtOAc, yielding the hydroxylamine.

Examples 36–40

Examples 36–40 are prepared using substantially the same procedure as that described in Example 35, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 36

11-hydroxylamino -17-phenyl-17-trinor-PGF$_{2a}$

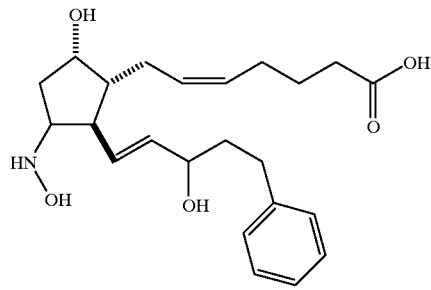

Example 37

11-hydroxylamino -15-R-methyl-PGF$_{2a}$

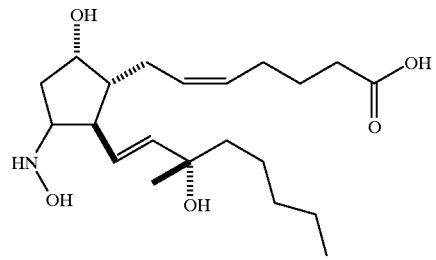

Example 38

11-methoxylamino-13,14-dihydro-17-(3,5-difluorophenyl)-17-trinor PGF$_{1a}$

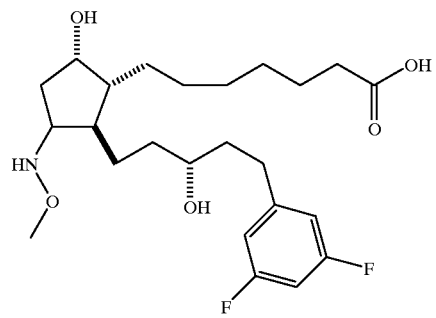

Example 39

11-hydroxylamino-13,14-dihydro-17-(3-furanyl)-17-trinor-PGF$_{1a}$

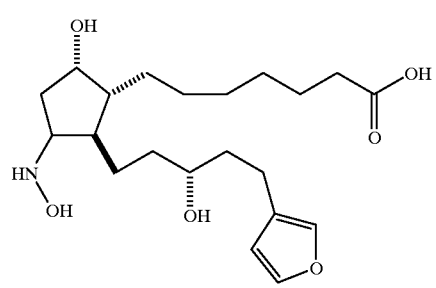

Example 40

11-hydroxylamino-13,14-dihydro-17-((3-trifluoromethyl)phenyl)-17-trinor PGF$_{1a}$ methyl ester

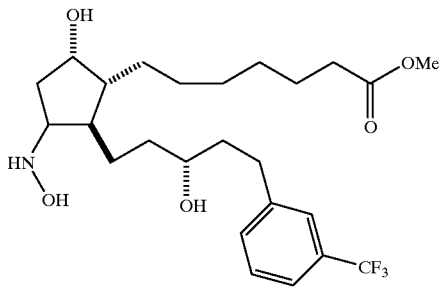

Example 41

11-oximyl-15-methyl-17-o-fluorophenyl-17-trinor-PGD$_2$ methyl ester

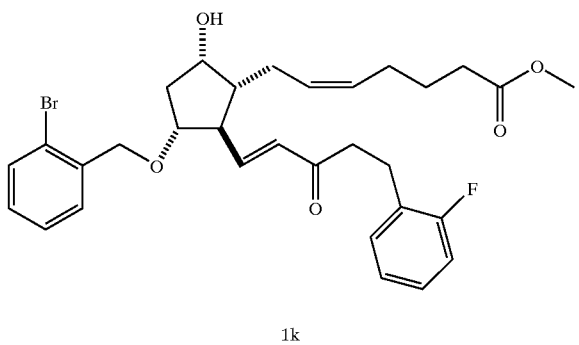

1k

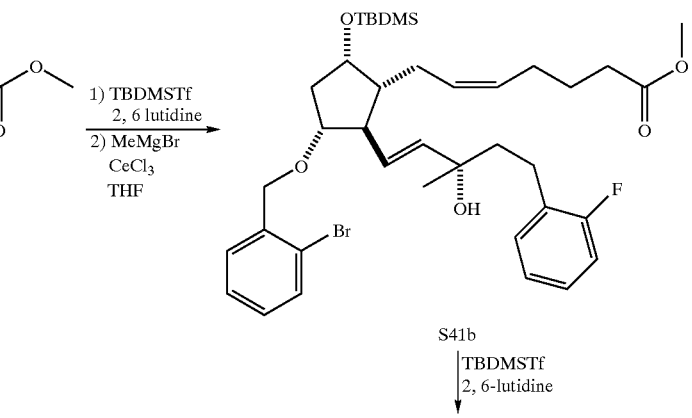

S41b

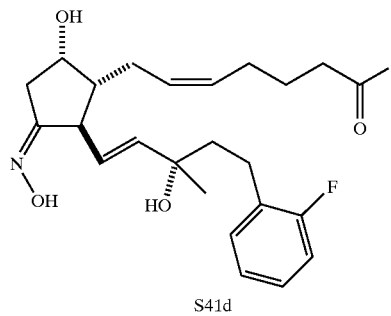

S41d

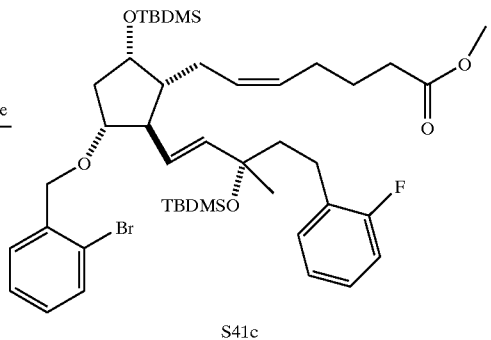

S41c

Compound 1k from Example 1 is dissolved in dry THF and 1.2 equiv. of TBDMSOTf and 1.5 equiv. of 2,6 lutidine are added. Standard work-up yields the TBDMS-protected version of 1k, which is dissolved in THF. Addition of the methylcerium nucleophile (~1.5 equiv.) (for examples of cerium chloride-mediated nucleophilic addition see: T. Imamoto, et al., "Carbon-Carbon Bond Forming Reactions Using Cerium Metal or Organocerium (III) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein) gives the product S41c, which after purification is dissolved in liquid ammonia and a sufficient amount of lithium metal is added to effect deprotection of the benzyl ether. After purification, the deprotected S41c is condensed with hydroxylamine as described in Example 1 and deprotected to yield the title compound, S41d.

Examples 42–43

Examples 42–43 are prepared using substantially the same procedure as that described in Example 41, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus within the scope of the invention.

Example 42

11-oximyl-15-ethyl-18-phenyl-18-dinor-PGD₂

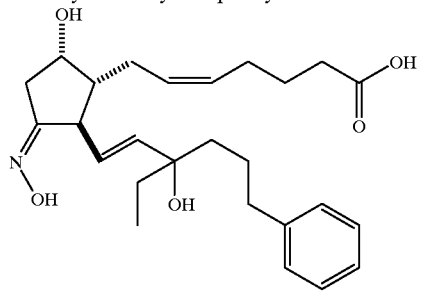

Example 43

3-oxo-11-oximyl-13,14-dihydro-15-methyl-17-phenyl-17-trinor-PGD₂

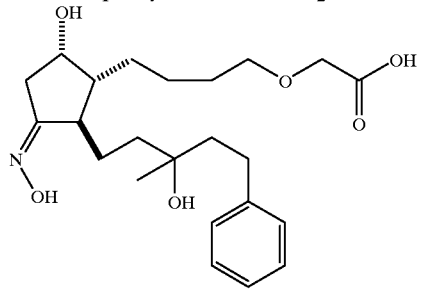

Example 44

3-oxo-11-hydroxylamino13,14-dihydro15methyl-15phenyl-17-trinor-PGF$_{2a}$

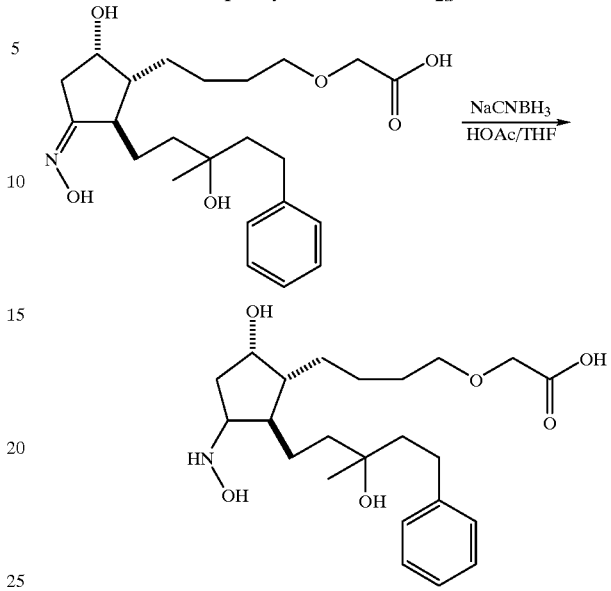

To a 50 mL round bottom flask is 3-oxo-11-oximyl-13,14-dihydro-15-methyl-17-phenyl-17-trinor-PGD₂ (Example 43) and 1.5 equiv. of sodium cyanoborohydride in a 1:1 mixture of acetic acid and tetrahydrofuran. The reaction is monitored by TLC. After complete consumption of starting material, the reaction is diluted with water, the pH is adjusted to 3.0, and exhaustively extracted with EtOAc, yielding the title hydroxylamine containing PGF analog.

Example 45
11-oximyl-15-methyl-15-deoxy-15-methamino-17-(2-fluorophenyl)-17-trinor-PGD₂ methyl ester

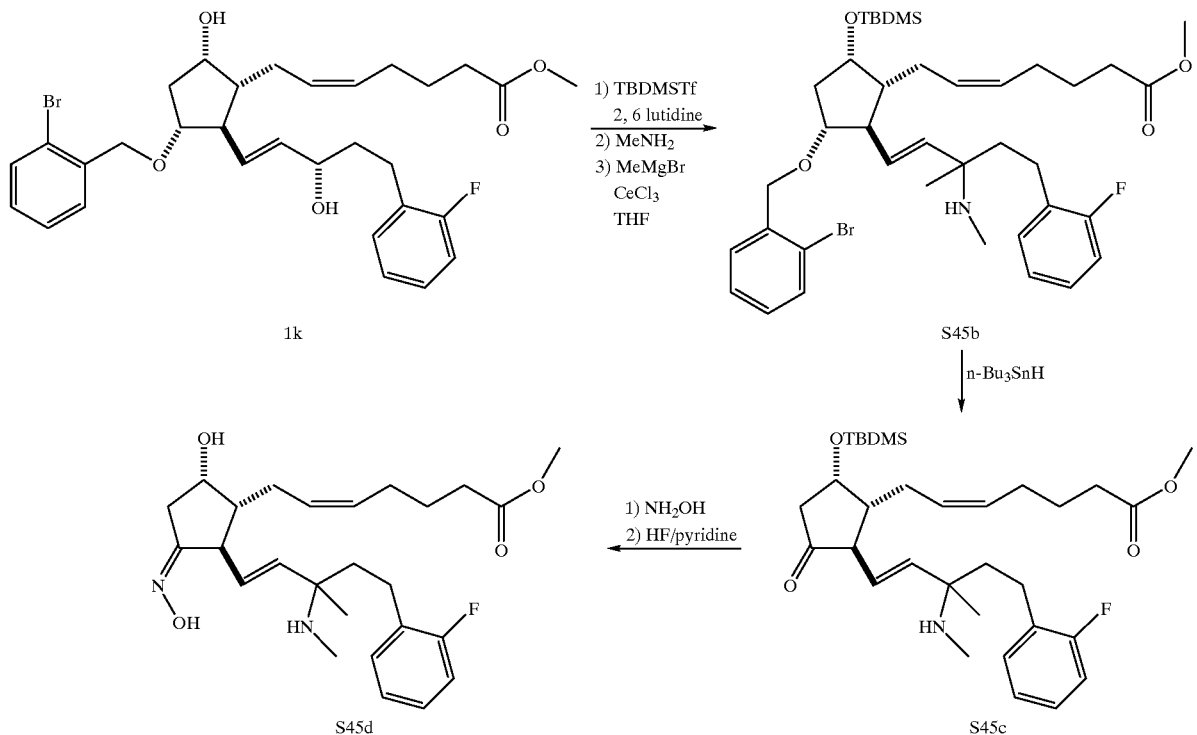

Compound 1k from Example 1 is dissolved in dry THF and 1.2 equiv. of TBDMSTf and 1.5 equiv. of 2,6 lutidine are added. Standard work-up yields the TBDMS-protected version of 1k, which is dissolved in THF and condensed with methylamine to give the intermediate imine. Addition of the methylcerium nucleophile (~1.5 equiv.) (for examples of cerium chloride-mediated nucleophilic addition see: T. Imamoto, et al., "Carbon-Carbon Bond Forming Reactions Using Cerium Metal or Organocerium (III) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein) gives the product S45b, which after purification is dissolved in THF and a sufficient amount of tri-n-butyl tin hydride is added to effect the oxidative removal of the benzyl ether. After purification, S45c is condensed with hydroxylamine as described in Example 1 and deprotected to yield the title compound, S45d.

Example 46

11-hydroxylamino-15-methyl-15-deoxy-15-methamino-17-(2-fluorophenyl)-17-trinor-PGF$_{2a}$ methyl ester

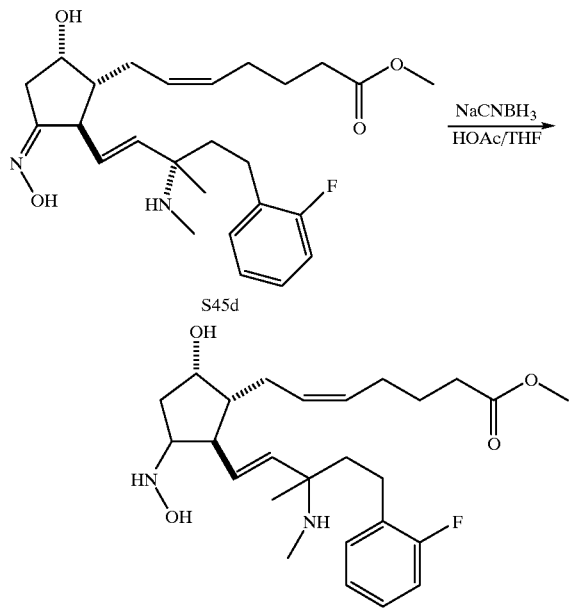

To a 50 mL round bottom flask is charged 11-oximyl-15-methyl-15-deoxy-15-methamino-17-o-fluorophenyl-17-trinor-PGD$_2$ methyl ester (Example 45) and 1.5 equiv. of sodium cyanoborohydride in a 1:1 mixture of acetic acid and tetrahydrofuran. The reaction is monitored by TLC. After complete consumption of starting material, the reaction is diluted with water and exhaustively extracted with EtOAc, yielding the title hydroxylamine containing PGF analog.

Example 47

11-oximyl-13,14-dihydro-17-((3-trifluoromethyl)phenyl)-17-trinor-PGD$_1$ 1-hydroxamic acid

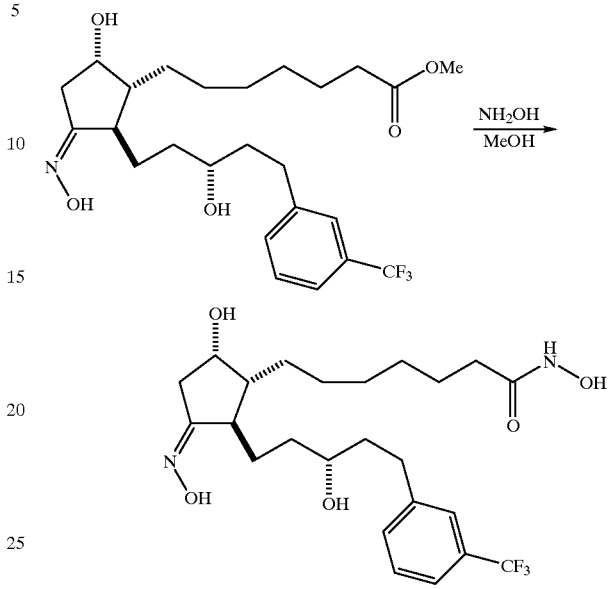

In a flame-dried 25 mL round-bottomed flask equipped with a magnetic stirbar is placed 11-oximyl-13,14-dihydro-17-((3-trifluoromethyl)phenyl)-17-trinor-PGD$_1$ methyl ester (Example 12) (1.0 equiv.) in methanol. To this solution is added hydroxylamine in methanol (1.25 equiv.). The solution is stirred for 18 hours. The solution is then treated with 1N hydrochloric acid and thrice extracted with ethyl acetate. The organic layer is washed with saturated aqueous sodium chloride, dried over anhydrous MgSO$_4$, filtered and concentrated under reduced pressure. The residue is purified by chromatography to give 11-oximyl-13,14-dihydro-17-((3-trifluoromethyl)phenyl)-17-trinor-PGD$_1$ 1-hydroxamic acid.

Examples 48 are prepared using substantially the same procedure as that described in Example 47, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 48

11-oximyl-17-phenyl-17-trinor-PGD$_2$ 1-N-methanesulfonamide

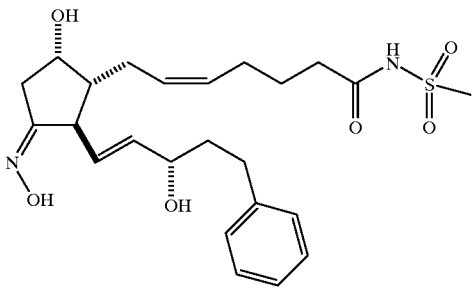

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing (1) bone volume and trabecular number through formation of new trabeculae, (2) bone mass while maintaining a normalized bone turnover rate, and/or (3) formation at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 $\mu$g/kg body weight, preferably from about 0.1 to about 100 $\mu$g/kg per body weight, most preferably form about 1 to about 50 $\mu$/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
| --- | --- |
| Compound of Example 1 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
| --- | --- |
| Compound of Example 32 | 1 mg |
| Phosphate buffered physiological saline | 10 ml |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
| --- | --- |
| Compound of Example 1 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

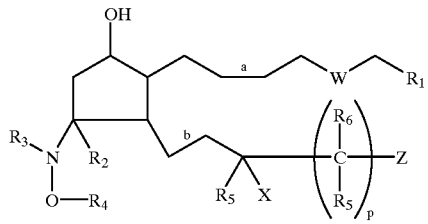

characterized in that (a) $R_1$ is $CO_2H$, $C(O)NHOH$, $CO_2R_7$, $CH_2OH$, $S(O)_2R_7$, $C(O)NHR_7$, $C(O)NHS(O)_2R_7$, or tetrazole; characterized in that $R_7$ is alkyl, heteroalkyl, monocyclic carbocyclic aliphatic ring, monocyclic heterocyclic aliphatic ring, monocyclic aromatic ring, or monocyclic heteroaromatic ring;

(b) W is O, NH, S, S(O), $S(O)_2$, or $(CH_2)_m$; characterized in that m is an integer from 0 to about 3;

(c) $R_2$ is H and $R_3$ is H or lower alkyl, or $R_2$ and $R_3$ together form a covalent bond;

(d) $R_4$ is H, alkyl, heteroalkyl, monocyclic carbocyclic aliphatic ring, monocyclic heterocyclic aliphatic ring, monocyclic aromatic ring, or monocyclic heteroaromatic ring, provided that when each $R_5$ and $R_6$ is H, $R_4$ is other than methyl;

(e) each $R_5$ is independently selected from the group consisting of H, $CH_3$, and $C_2H_5$;

(f) X is $NHR_8$ or $OR_8$, characterized in that each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring;

(g) each $R_6$ is independently selected from the group consisting of H, $CH_3$, $C_2H_5$, $OR_8$, and $NHR_8$;

(h) Z is H, methyl, monocyclic carbocyclic aliphatic ring, monocyclic heterocyclic aliphatic ring, monocyclic aromatic ring, monocyclic heteroaromatic ring, bicyclic carbocyclic aliphatic ring, bicyclic heterocyclic aliphatic ring, bicyclic aromatic ring, or bicyclic heteroaromatic ring;

(i) a and b are independently selected from the group consisting of single bond, cis double bond, and trans double bond;

(j) p is an integer from 0 to 6; and any optical isomer, diastereomer, enantiomer of the above structure or a pharmaceutically-acceptable salt, or biohydrolyzable amide, ester, or imide thereof.

2. The compound of claim 1 wherein $R_1$ is $CO_2H$, $C(O)NHOH$, $CO_2R_7$, $C(O)NHS(O)_2R_7$, or tetrazole.

3. The compound of claim 2 wherein W is O or $(CH_2)_m$.

4. The compound of claim 3 wherein p is 2 or 3.

5. The compound of claim 4 wherein Z is monocyclic aromatic ring or monocyclic heteroaromatic ring.

6. The compound of claim 5 wherein $R_4$ and $R_5$ are each H and X is OH.

7. The compound of claim 6 wherein $R_1$ is $CO_2H$ or $CO_2R_7$.

8. The compound of claim 7 wherein W is $(CH_2)_1$.

9. The compound of claim 8 wherein p is 2.

10. The compound of claim 9 wherein Z is phenyl.

11. The compound of claim 10 wherein a is a cis double bond and b is a trans double bond.

12. The compound of claim 11 wherein $R_2$ and $R_3$ are both H.

13. The compound of claim 11 wherein $R_2$ and $R_3$ together form a double bond.

14. A method of treating a human or other animal subject having a bone disorder, said method comprising administering to said subject a compound according to the structure:

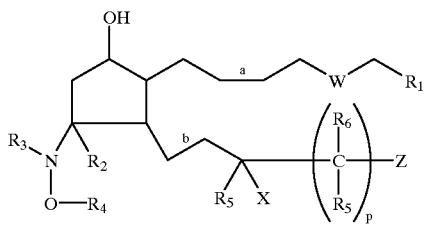

wherein
(a) $R_1$ is $CO_2H$, $C(O)NHOH$, $CO_2R_7$, $CH_2OH$, $S(O)_2R_7$, $C(O)NHR_7$, $C(O)NHS(O)_2R_7$, or tetrazole; wherein $R_7$ is alkyl, heteroalkyl, monocyclic carbocyclic aliphatic ring, monocyclic heterocyclic aliphatic ring, monocyclic aromatic ring, or monocyclic heteroaromatic ring;
(b) W is O, NH, S, S(O), $S(O)_2$, or $(CH_2)_m$; wherein m is an integer from 0 to about 3;
(c) $R_2$ is H and $R_3$ is H or lower alkyl, or $R_2$ and $R_3$ together form a covalent bond;
(d) $R_4$ is H, alkyl, heteroalkyl, monocyclic carbocyclic aliphatic ring, monocyclic heterocyclic aliphatic ring, monocyclic aromatic ring, or monocyclic heteroaromatic ring, provided that when each $R_5$ and $R_6$ is H, $R_4$ is other than methyl;
(e) each $R_5$ is independently selected from the group consisting of H, $CH_3$, and $C_2H_5$;
(f) X is $NHR_8$ or $OR_8$, wherein each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring;
(g) each $R_6$ is independently selected from the group consisting of H, $CH_3$, $C_2H_5$, $OR_8$, and $NHR_8$;
(h) Z is H, methyl, monocyclic carbocyclic aliphatic ring, monocyclic heterocyclic aliphatic ring, monocyclic aromatic ring, monocyclic heteroaromatic ring, bicyclic carbocyclic aliphatic ring, bicyclic heterocyclic aliphatic ring, bicyclic aromatic ring, or bicyclic heteroaromatic ring;
(i) a and b are independently selected from the group consisting of single bond, c is double bond, and trans double bond;
(j) p is an integer from 0 to about 6; and
any optical isomer, diastereomer, enantiomer of the above structure or a pharmaceutically-acceptable salt, or biohydrolyzable amide, ester, or imide thereof.

15. The method of claim 14 wherein said bone disorder is osteoporosis.

16. The method of claim 15 wherein in osteoporosis is post-menopausal.

17. The method of claim 15 wherein in osteoporosis is cortico-steroid induced.

18. The method of claim 14 wherein said bone disorder is osteopenia.

19. The method of claim 14 wherein said bone disorder is a bone fracture.

20. The method of claim 14 wherein said compound is administered orally.

21. The method of claim 14 wherein said compound is administered transdermally.

22. The method of claim 14 wherein said compound is administered intranasally.

23. A method of treating glaucoma, said method comprising administering to a human or other animal a safe and effective amount of a compound according to the structure:

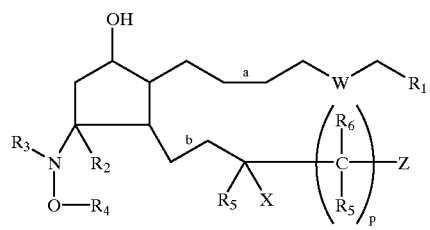

wherein
(a) $R_1$ is $CO_2H$, $C(O)NHOH$, $CO_2R_7$, $CH_2OH$, $S(O)_2R_7$, $C(O)NHR_7$, $C(O)NHS(O)_2R_7$, or tetrazole; wherein $R_7$ is alkyl, heteroalkyl, monocyclic carbocyclic aliphatic ring, monocyclic heterocyclic aliphatic ring, monocyclic aromatic ring, or monocyclic heteroaromatic ring;
(b) W is O, NH, S, S(O), $S(O)_2$, or $(CH_2)_m$; wherein m is an integer from 0 to about 3;
(c) $R_2$ is H and $R_3$ is H or lower alkyl, or $R_2$ and $R_3$ together form a covalent bond;
(d) $R_4$ is H, alkyl, heteroalkyl, monocyclic carbocyclic aliphatic ring, monocyclic heterocyclic aliphatic ring, monocyclic aromatic ring, or monocyclic heteroaromatic ring, provided that when each $R_5$ and $R_6$ is H, $R_4$ is other than methyl;
(e) each $R_5$ is independently selected from the group consisting of H, $CH_3$, and $C_2H_5$;
(f) X is $NHR_8$ or $OR_8$, wherein each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring;
(g) each $R_6$ is independently selected from the group consisting of H, $CH_3$, $C_2H_5$, $OR_8$, and $NHR_8$;
(h) Z is H, methyl, monocyclic carbocyclic aliphatic ring, monocyclic heterocyclic aliphatic ring, monocyclic aromatic ring, monocyclic heteroaromatic ring, bicyclic carbocyclic aliphatic ring, bicyclic heterocyclic aliphatic ring, bicyclic aromatic ring, or bicyclic heteroaromatic ring;
(i) a and b are independently selected from the group consisting of single bond, cis double bond, and trans double bond;
(j) p is an integer from 0 to about 6; and
any optical isomer, diastereomer, enantiomer of the above structure or a pharmaceutically-acceptable salt, or biohydrolyzable amide, ester, or imide thereof.

24. The method of claim 23 wherein said compound is administered topically.

* * * * *

UNITED STATES PATENT AND TRADEMARK OFFICE
CERTIFICATE OF CORRECTION

PATENT NO.      : 6,410,780 B1
DATED           : June 25, 2002
INVENTOR(S)     : Mitchell Anthony deLong et al.

It is certified that error appears in the above-identified patent and that said Letters Patent is hereby corrected as shown below:

<u>Column 5,</u>
Line 32, delete "$SO_2R_7$" and insert -- $S(O)_2R_7$ --.

<u>Column 12,</u>
Example 1, delete "o-Br-benzl" and insert -- o-Br-benzyl --.

<u>Column 15,</u>
Line 10, delete "-hydroxy4" and insert -- hydroxy-4 --.

<u>Column 19,</u>
Example 7, delete "-fluoro5-" and insert -- fluoro-5 --.
Example 8, delete "3fluorophenyl" and insert -- 3-flurophenyl --.

Signed and Sealed this

Thirtieth Day of December, 2003

JAMES E. ROGAN
*Director of the United States Patent and Trademark Office*